(12) United States Patent
Rose et al.

(10) Patent No.: US 12,197,878 B1
(45) Date of Patent: Jan. 14, 2025

(54) SYSTEMS AND METHODS FOR PROVIDING REAL-TIME RECOMMENDATIONS USING NATURAL LANGUAGE PROCESSING

(71) Applicant: Included Health, Inc., San Francisco, CA (US)

(72) Inventors: Peyton Rose, San Francisco, CA (US); Matt Forbes, San Francisco, CA (US); Susan Enneking, San Francisco, CA (US); Jack Sullivan, San Francisco, CA (US); Jennifer Kong, San Francisco, CA (US)

(73) Assignee: Included Health, Inc., San Francisco, CA (US)

( * ) Notice: Subject to any disclaimer, the term of this patent is extended or adjusted under 35 U.S.C. 154(b) by 0 days.

(21) Appl. No.: 18/451,046

(22) Filed: Aug. 16, 2023

(51) Int. Cl.
*G06F 40/40* (2020.01)
*G06F 3/0482* (2013.01)
*G06Q 40/08* (2012.01)
*G16H 20/00* (2018.01)

(52) U.S. Cl.
CPC .......... *G06F 40/40* (2020.01); *G06F 3/0482* (2013.01); *G06Q 40/08* (2013.01); *G16H 20/00* (2018.01)

(58) Field of Classification Search
CPC ....... G06F 40/40; G06F 3/0482; G06Q 40/08; G16H 20/00
USPC .......................................................... 704/9
See application file for complete search history.

(56) References Cited

U.S. PATENT DOCUMENTS

| | | | |
|---|---|---|---|
| 11,620,718 B1 * | 4/2023 | Babbar ................. | G16H 10/60 705/4 |
| 2019/0073412 A1 * | 3/2019 | Ranganathan ...... | G06F 16/9035 |

* cited by examiner

*Primary Examiner* — Thierry L Pham
(74) *Attorney, Agent, or Firm* — FINNEGAN, HENDERSON, FARABOW, GARRETT & DUNNER, LLP

(57) ABSTRACT

Methods, systems, and computer-readable media for the generation of real-time recommendations using natural language processing. The method receives a request for a benefit recommendation; generates at least one tag based on input data; extracts, based on the at least one tag, at least one observation and at least one action from the input data; predicts at least one recommendation based on the extracted at least one observation and the extracted at least one action in real time; and sends the at least one predicted recommendation for display to a user device.

20 Claims, 8 Drawing Sheets

SYSTEMS AND METHODS FOR PROVIDING REAL-TIME RECOMMENDATIONS USING NATURAL LANGUAGE PROCESSING

BACKGROUND

An ever increasing amount of data and data sources are now available to researchers, analysts, organizational entities, and others. This influx of information allows for sophisticated analysis but, at the same time, presents many new challenges for sifting through the available data and data sources to locate the most relevant and useful information. As the use of technology continues to increase, so, too, will the availability of new data sources and information.

Because of the abundant availability of data from a vast number of data sources, determining the optimal values and sources for use presents a complicated problem difficult to overcome. Accurately utilizing the available data can require both a team of individuals possessing extensive domain expertise as well as many months of work to evaluate the outcomes. The process can involve exhaustively searching existing literature, publications, and other available data to identify and study relevant data sources that are available both privately and publicly.

While this approach can often provide effective academic analysis, applying these types of analytical techniques to domains requiring accurate results obtainable only through time and resource intensive research is incompatible with modern applications' demands. For example, the developed process for evaluating outcomes may not line up with specific circumstances or individual considerations. In this scenario, applying the process requires extrapolation to fit the specific circumstances, to dilute the process's effectiveness, or to require spending valuable time and resources to modify the process. As a result, processes developed in this way typically provide only generalized guidance insufficient for repurposing in other settings or by other users. As more detailed and individualized data becomes available, demand for the ability to accurately discern relevant data points from the sea of available information, and efficiently apply that data across thousands of personalized scenarios increases.

SUMMARY

Certain embodiments of the present disclosure relate to a system for generating a real-time recommendation. The system includes one or more processors executing processor-executable instructions stored in one or more memory devices. The instructions may include receiving a request for a benefit recommendation; generating at least one tag based on input data; extracting, based on the at least one tag, at least one observation and at least one action from the input data; predicting at least one recommendation based on the extracted at least one observation and the extracted at least one action in real time; and sending the at least one predicted recommendation for display to a user device.

According to some disclosed embodiments, the request may be made by a service provider.

According to some disclosed embodiments, the predicting may further comprise predicting by a recommendation engine and determining a number of observation edges associated with at least one action and mapping the number of observation edges a list of benefits.

According to some disclosed embodiments, the operations may further comprise ranking the at least one action based on the observation edges to determine the at least one recommendation.

According to some disclosed embodiments, the ranking may further comprise ranking the at least one action with the least amount of observation edges as the highest.

According to some disclosed embodiments, the ranking may further comprise using mapping data based on the at least one observation and the at least one action to determine a recommendation.

According to some disclosed embodiments, the generating may further comprise using a natural language processing engine.

According to some disclosed embodiments, the natural language processing engine may use a machine learning platform to generate tags.

According to some disclosed embodiments, the system may further comprise a browser plug in to receive the request for a recommendation.

According to some disclosed embodiments, the predicting may be based on pre-configured rules.

Certain embodiments of the present disclosure relate to a method performed by a system for generating a real-time recommendation. The method may include receiving a request for a benefit recommendation; generating at least one tag based on input data; extracting, based on the at least one tag, at least one observation and at least one action from the input data; predicting at least one recommendation based on the extracted at least one observation and the extracted at least one action in real time; and sending the at least one predicted recommendation for display to a user device.

Certain embodiments of the present disclosure relate to a non-transitory computer readable medium including instructions that are executable by one or more processors to cause a system to perform a method for generating a real-time recommendation. The method may include receiving a request for a benefit recommendation; generating at least one tag based on input data; extracting, based on the at least one tag, at least one observation and at least one action from the input data; predicting at least one recommendation based on the extracted at least one observation and the extracted at least one action in real time; and sending the at least one predicted recommendation for display to a user device.

BRIEF DESCRIPTION OF THE DRAWINGS

The accompanying drawings, which are incorporated in and constitute a part of this specification, illustrate several embodiments and, together with the description, serve to explain the disclosed principles. In the drawings.

DETAILED DESCRIPTION

Figure 1:
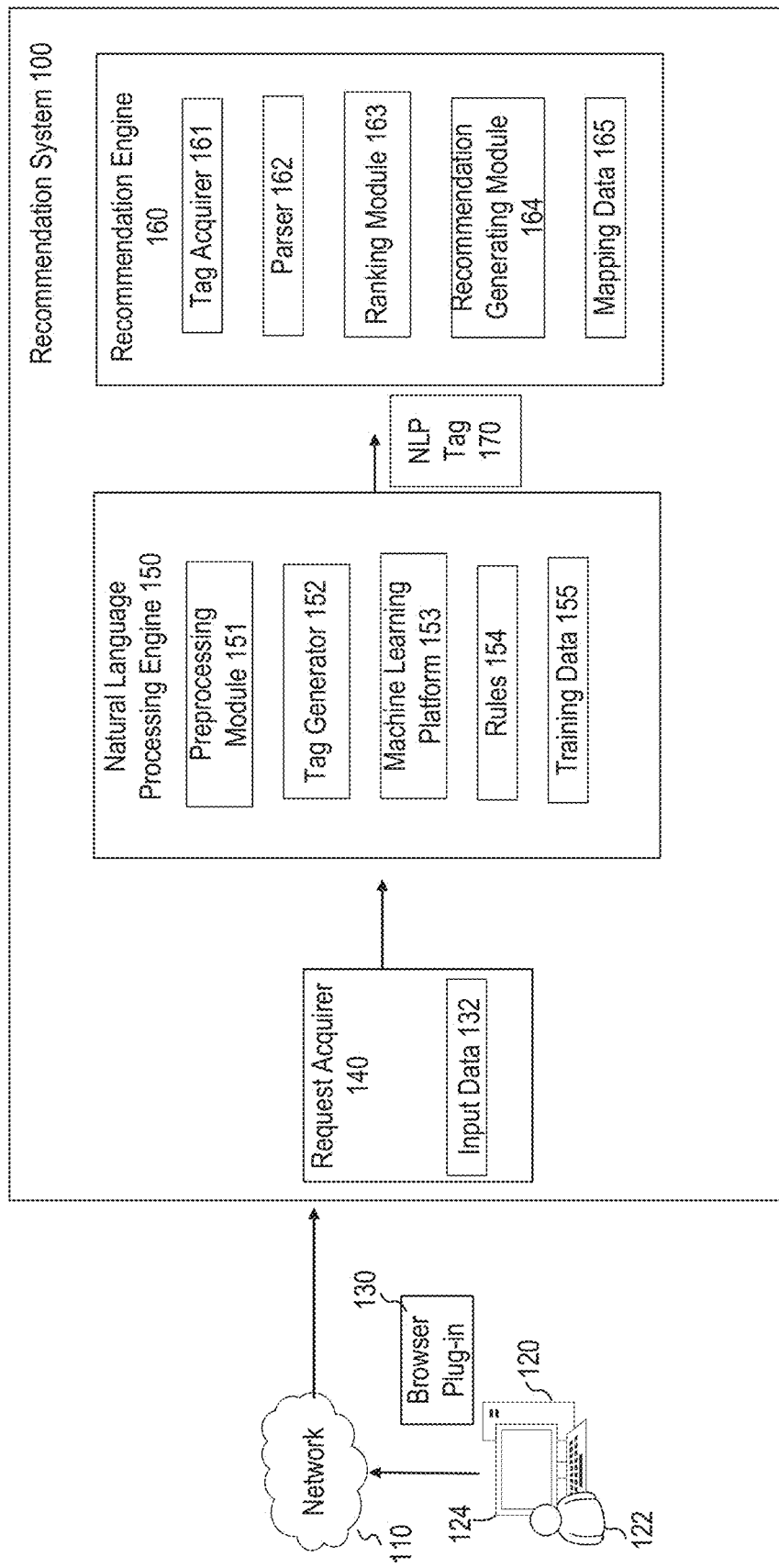
FIG. 1 is a block diagram showing various exemplary components of a real-time recommendation system, according to some embodiments of the present disclosure.

In the following detailed description, numerous specific details are set forth in order to provide a thorough understanding of the disclosed example embodiments. However, it will be understood by those skilled in the art that the principles of the example embodiments may be practiced without every specific detail. Well-known methods, procedures, and components have not been described in detail so as not to obscure the principles of the example embodiments. Unless explicitly stated, the example methods and processes described herein are neither constrained to a particular order or sequence nor constrained to a particular system configuration. Additionally, some of the described embodiments or elements thereof can occur or be performed simultaneously, at the same point in time, or concurrently. Reference will now be made in detail to the disclosed embodiments, examples of which are illustrated in the accompanying drawings. Unless explicitly stated, sending and receiving as used herein are understood to have broad meanings, including sending or receiving in response to a specific request or without such a specific request. These terms thus cover both active forms, and passive forms, of sending and receiving.

The embodiments described herein provide technologies and techniques for evaluating large numbers of data sources and vast amounts of data used in the creation of a machine learning model. These technologies can use information relevant to the specific domain and application of a machine learning model to prioritize potential data sources. Further, the technologies and techniques herein can interpret the available data sources and data to extract probabilities and outcomes associated with the machine learning model's specific domain and application. The described technologies can synthesize the data into a coherent machine learning model, that can be used to analyze and compare various paths or courses of action.

These technologies can efficiently evaluate data sources and data, prioritize their importance based on domain and circumstance specific needs, and provide effective and accurate predictions that can be used to evaluate potential courses of action. The technologies and methods allow for the application of data models to personalized circumstances. These methods and technologies allow for detailed evaluation that can improve decision making on a case-by-case basis. Further, these technologies can evaluate a system where the process for evaluating outcomes of data may be set up easily and repurposed by other uses of the technologies.

Technologies may utilize machine learning models to automate the process and predict responses without human intervention. The performance of such machine learning models is usually improved by providing more training data. A machine learning model's prediction quality is evaluated manually to determine if the machine learning model needs further training. Embodiments of these technologies described can help improve machine learning model predictions using the quality metrics of predictions requested by a user.

FIG. 1 is a block diagram showing various exemplary components of a real-time recommendation system, according to some embodiments of the present disclosure. FIG. 1 illustrates an example recommendation system 100 for securely providing recommendations based on prediction, consistent with the disclosed embodiments. As shown in FIG. 1, recommendation system 100 may include a request acquirer 140, a natural language processing engine 150, and a recommendation engine 160. In some embodiments, recommendation system 100 is configured to provide recommendation(s) upon receiving a request for recommendation. In some embodiments, recommendation system 100 may further include user device 120. In some embodiments, recommendation system 100 may further include browser plug-in 130. FIG. 1 also illustrates user 122 that may interact with recommendation system 100.

As shown in FIG. 1, the various components of recommendation system 100 may communicate over a network 110. Such communications may take place across various types of networks, such as the Internet, a wired Wide Area Network (WAN), a wired Local Area Network (LAN), a wireless WAN (e.g., WiMAX), a wireless LAN (e.g., IEEE 802.11, etc.), a mesh network, a mobile/cellular network, an enterprise or private data network, a storage area network, a virtual private network using a public network, a nearfield communications technique (e.g., Bluetooth, infrared, etc.), or various other types of network communications. In some embodiments, the communications may take place across two or more of these forms of networks and protocols. While recommendation system 100 is shown as a network-based environment, it is understood that in some embodiments, one or more aspects of the disclosed systems and methods may also be used in a localized system, with one or more of the components communicating directly with each other.

Request acquirer 140 may acquire a request for recommendation, consistent with some embodiments of the present disclosure. In some embodiments, request acquirer 140 may receive a request for recommendation from user device 120 as shown in FIG. 1. Recommendation system 100 may represent a system or network environment in which user 122 can request and receive a recommendation in real time via user device 120. In some embodiments, activities of user 122 may be recorded and stored on a server, such as server 510, described in greater detail with respect to FIG. 5.

User device 120 may include any form of computer-based device or entity through which user 122 may interact with recommendation system 100, e.g., via browser plug-in 130. For example, user device 120 may be a personal computer (e.g., a desktop or laptop computer), a mobile device (e.g., a mobile phone or tablet), or any other device that may be capable of accessing web pages or other network locations. In some embodiments, user device 120 may be a virtual machine (e.g., based on AWS™, Azure™, IBM Cloud™, etc.), container instance (e.g., Docker™ container, Java™ container, Windows Server™ container, etc.), or other virtualized instance. User device 120 may be configured such that user 122 may access a browser plug-in 130 through a browser or other software executing on user device 120. In some embodiments, user device 120 can be configured to generate a request for recommendation. In some embodiments, user device 120 can be configured to generate a request for recommendation in response to user interaction with user device 120. In some embodiments, user interaction can include user's input to user device 120. In some embodiments, a request for recommendation can be a request for service recommendation.

In some embodiments, user device 120 is provided with user interface 124. In some embodiments, user interface 124 enables user 122 to input data to user device 120. In some embodiments, user 122 can be an agent that can provide service recommendation(s) to a member. For example, in a healthcare setting, user 122 can be a healthcare worker or staff such as a doctor, nurse, consultant, adviser, etc. In a healthcare setting, input data can be patient information such as medical conditions, symptoms, sufferings, etc. In some embodiments, user 122 can input information to user device 120 via user interface 124. In some embodiments, information inputted to user device 120 can be in various formats. In some embodiments, user interface 124 can be configured to acquire various formats of user input. For example, user interface 124 can include a keyboard and a display such that user 122 can type information via a keyboard in a designated area on the display. User interface 124 can also include a microphone through which user's speech can be inputted to user device 120. Activities of user 122 may comprise taking notes on user interface 124 in real-time. User interface 124 is further described with respect to FIG. 4. For instance, under a healthcare setting, a doctor can take notes with user device 120 while consulting with a member. In a non-limiting example, a member may be a patient in a healthcare setting. Examples of notes user 122 takes may include notes related to a member's symptoms, a member's presentation, changes in a member since their last visit, such as changes to a member's presentation, additional or different symptoms, or any changes a provider indicates is relevant at the time, response to treatment recommendations, assessment of the member, results of a physical examination, diagnostic test results, potential diagnosis, overall assessment information, etc. In some embodiments, these notes comprise input data 132. In some embodiments, notes user 122 takes on user device 120 can be recorded to provide an accurate record of all notes associated with a particular member. User 122 may then view these recordings on user device 120 for a comprehensive member history. The recording, transmission, and storage of the recorded member notes may be performed in a secure manner, such that only qualified personnel or device such as user device 120 can have access to the recorded information.

According to some embodiments, browser plug-in 130 can be configured to forward input data to request acquirer 140. In some embodiments, browser plug-in 130 can be configured to collect and forward texts in a designated area on the display of user device 120 as input data. In some embodiments, browser plug-in 130 can be configured to collect and forward speech data received from user 122 as input data. In some embodiments, browser plug-in 130 can forward input data to request acquirer 140 in response to user's action, e.g., clicking a certain button on a display, user's voice command, etc. In some embodiments, browser plug-in 130 can be configured to continuously monitor whether new input data is inputted to user device 120 and to forward the new input data as it comes into user device 120. In some embodiments, browser plug-in 130 can periodically check whether new input data is inputted by user 122 and to forward the new input data.

In some embodiments, browser plug-in 130 may be installed on an apparatus, such as user device 120, via a web browser. In some embodiments, browser plug-in 130 may be configured to alter the functionality of the web browser. In some embodiments browser plug-in 130 may be encrypted to protect confidential information. In some embodiments, browser plug-in 130 may be enabled for recommendation system 100 to function properly. In some embodiments, browser plug-in 130 adds additional functionality to a web browser and operates as an integrated part of the web browser. For example, browser plug-in 130 may provide user 122 access to additional functionality by modifying user interface 124 of a web browser. As a non-limiting example, browser plug-in 130 may be added to a browser, where the plug-in facilitates access to user interface 124 and use of recommendation system 100 by adding an icon or button to the UI of the browser. User 122 may then interact with the button or icon provided via browser plug-in 130 to obtain recommendation information. In some embodiments, browser plug-in 130 may be configured to receive data from user interface 124 in real time and configure the data for use. In some embodiments, browser plug-in 130 may be packaged as an installable entity. In some embodiments, a user may be prompted to install browser plug-in 130 on user device 120 when user 122 begins a process for recommendation system 100 for the first time. In other embodiments, the installation may occur automatically. In some embodiments, browser plug-in 130 may send input data to request acquirer 140 over network 110. While some embodiments are described that recommendation system 100 utilizes browser plug-in 130, it will be appreciated that collecting and forwarding of input data 132 can be implemented with any other technologies that can provide the similar functionalities of the browser plug-in described above.

According to some embodiments, request acquirer 140 may acquire input data from multiple sources. In some embodiments, request acquirer 140 may acquire input data 132 from user device 120, e.g., via browser plug-in 130. In some embodiments, input data 132 may comprise input data that user device 120 acquires from user 122. In some embodiments, when request acquirer 140 receives input data 132, e.g., which is pushed from user device 120, request acquirer 140 may consider such data push a request for recommendation. In some embodiments, for request acquirer 140 to obtain input data 132, browser plug-in 130 can be enabled. Input data 132 may be input data such as notes that user 122 took on user device 120, as previously described. In some embodiments, request acquirer 140 acquires input data 132 in real-time. In some embodiments, input data 132 may be related to a specific member.

According to some embodiments, natural language processing (NLP) engine 150 may include preprocessing module 151, tag generator 152, and machine learning platform 153. In some embodiments, NLP engine 150 can also include rules 154 and training data 155. In some embodiments, recommendation system 100 may also include one or more natural language processing engine 150, which can be distributed in a system.

Natural language processing (NLP) gives computers the ability to understand text and spoken words in the same way that humans can. NLP combines rule-based modeling of human language, known as computational linguistics, with statistical, machine learning, and deep learning models to help computers process human language, with the intention that the computer will understand both the language itself and the language's intent and sentiment. And NLP systems can assist with tasks including text translation, document retrieval and routing, and information extraction. The ability for NLP systems to understand nuances makes them more functional than conventional lookup tools. As a non-limiting example, conventional medical applications related to processing provider notes largely rely on search tools to retrieve medical codes that are applicable to member care. These conventional tools may rely on using search terms with basic search functionality. Therefore, a solution is needed to parse large documents and be able to pull the relevant information for interpretation. In particular, there is no known solution that uses an NLP processing engine to provide recommendations in real time related to healthcare services, insurance benefits, etc. based on the content of a provider's notes.

In some embodiments, NLP engine 150 may receive input data 132 from request acquirer 140. The data may be, in an unstructured or structured format. In some embodiments, NLP engine 150 may pre-process input data 132 using preprocessing module 151. In some embodiments, preprocessing module 151 can perform one or more pre-processing algorithms on input data 132 such that input data 132 can be recognized by machine. In some embodiments, preprocessing module 151 may remove punctuation from input data 132. In some embodiments, preprocessing module 151 may perform tokenization on input data 132. Tokenization separates text into units such as sentences or words. In some embodiments, preprocessing module 151 may remove stop words from input data 132. For example, preprocessing module 151 may remove common words such as "a, the, and" from input data 132. In some embodiments, preprocessing module 151 may perform stemming. Stemming may reduce a word to stem form by removing suffixes using a rule-based approach. Stemming may also treat words with the same stem as synonyms. In some embodiments, preprocessing module 151 may lemmatize input data 132 by deriving the root form of the word. In some embodiments, preprocessing module 151 may vectorize input data 132, which encodes text as integers to create feature vectors so that machine learning algorithms can understand language.

According to some embodiments of the present disclosure, once input data 132 is pre-processed by preprocessing module 151, tag generator 152 can generate one or more tags from the pre-processed input data. In some embodiments, tag generator 152 may generate one or more tags based on input data that is not pre-processed. Here, input data 132 can also refer to input data 132 that has been processed by preprocessing module 151. Generating NLP tags 170 may be based on data received by recommendation system 100 from request acquirer 140. In some embodiments, generating NLP tags 170 may be based on only clinical data. In other embodiments, generating NLP tags 170 may be based only on non-clinical data. In other embodiments, generating NLP tags 170 may be based on both clinical and nonclinical data. In some embodiments, tag generator 152 is configured to extract keywords from input data 132. Keyword extraction is a text analysis technique that may comprise automatically extracting the most used and most important words from input data 132. In some embodiments, tag generator 152 may extract one or more keywords from recognized text in input data 132.

Figure 3A:
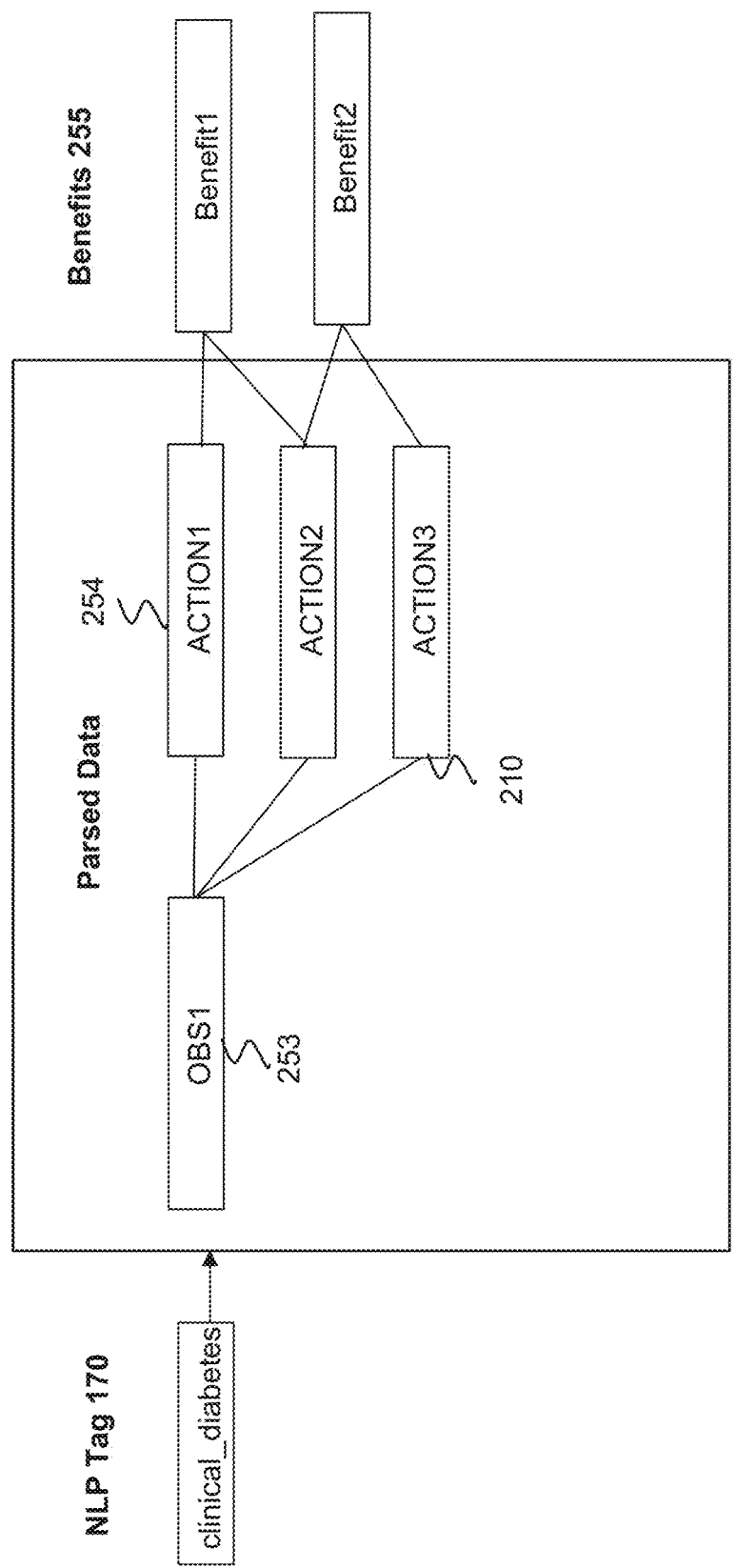
FIG. 3A is an exemplary flow diagram for providing recommendation(s), according to some embodiments of the present disclosure.
Figure 3B:
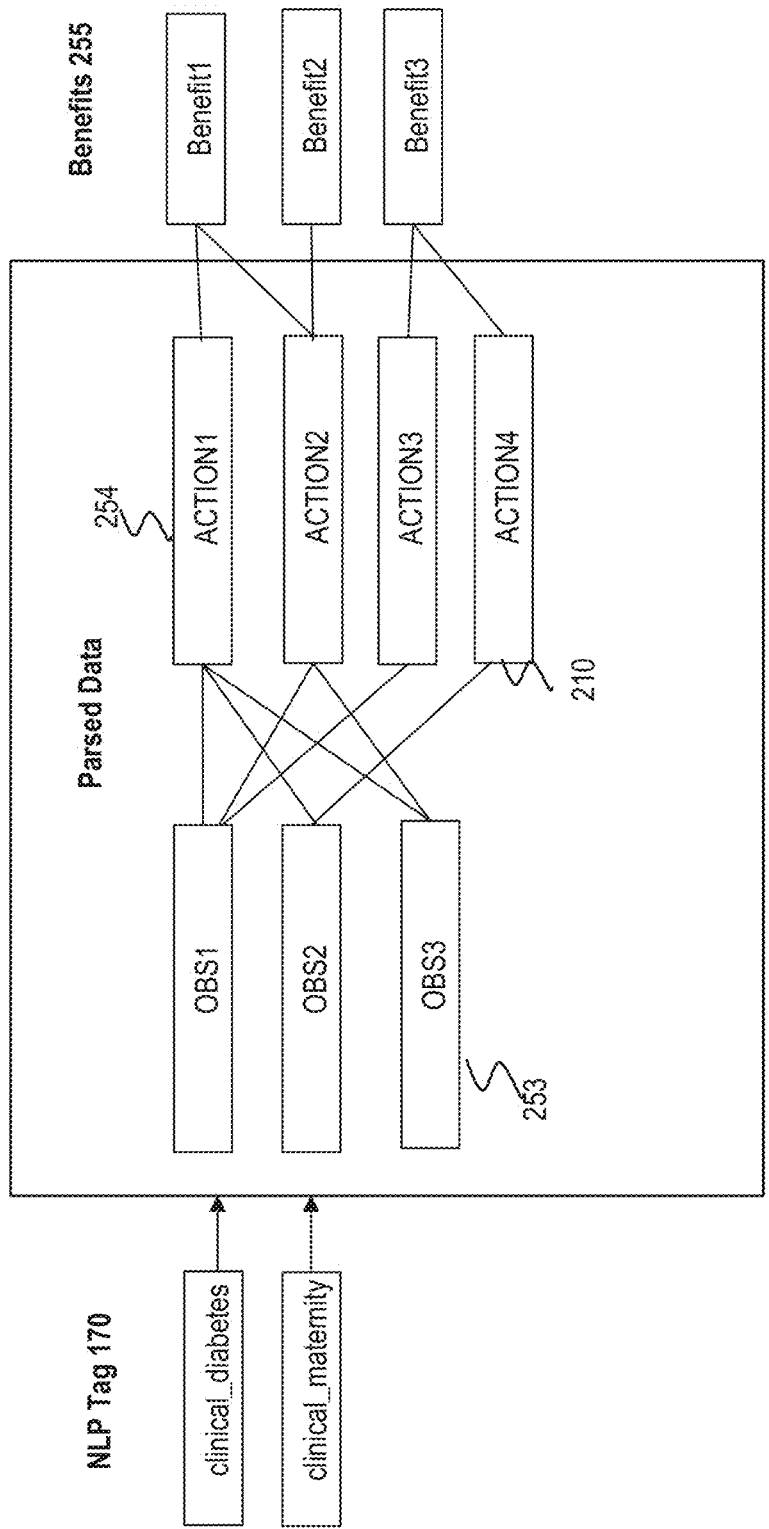
FIG. 3B is another exemplary flow diagram for providing recommendation(s), according to some embodiments of the present disclosure.

In some embodiments, tag generator 152 may be configured to identify one or more conditions based on the extracted keywords. In some embodiments, the identified conditions may be generated as NLP tags 170, such as clinical_diabetes or clinical_maternity, as shown in FIG. 3A or FIG. 3B. In some embodiments where the extracted one or more keywords include one or more conditions, tag generator 152 can generate the one or more conditions as NLP tag(s). In some embodiments where the extracted one or more keywords include one or more condition indicators, tag generator 152 can analyze which condition the one or more condition indicators indicate. In this example, tag generator 152 can generate the condition that is determined to be indicated by the extracted keywords as NLP tag(s). In some embodiments where one or more condition indicators can indicate one or more conditions, tag generator 152 can generate the indicated one or more condition as NLP tag(s). For example, if input data 132 contains keyword "pregnancy", tag generator 152 may generate NLP tags 170 related to pregnancy.

In some embodiments, NLP engine 150 may also include machine learning platform 153 to help generate tags from input data 132. In some embodiments, a machine learning algorithm(s) of machine learning platform 153 can be trained using rules 154 and training data 155. In some embodiments, training data 155 may be fed into NLP engine 150 from an external source, such as a server, database, sensor or Internet of Things device. The performance of machine learning platform 153 can be improved by providing more training data. Training data 155 may comprise member data related to all member in recommendation system 100. Training data 155 may comprise electronic medical records (EMR) that includes both clinical and nonclinical data. The clinical data may comprise data received from organizations such as hospitals, pharmacies, private providers, and clinics. The clinical data may comprise health information including physiological data, historical record data such as physical exams, medical history, family medical history, surgical history, emergency room records, pharmaceutical records, clinical notes, vaccination records, and any other physician notes. Nonclinical data may include demographic information, medical insurance information, employment information, lifestyle information such as diet and substance abuse nation, marital status, education, and contact information. In some embodiments, machine learning algorithm can be trained supervised, semi-supervised, or unsupervised.

In some embodiments, rules 154 may comprise a list of conditions that can be generated as an NLP tag 170. In some embodiments, the list of conditions can be predefined. For example, conditions may include medical conditions such as maternity, diabetes, etc. Rules 154 may be predefined and used by tag generator 152 to generate NLP tags 170. In some embodiments, rules 154 may include a list of keywords or a list of condition indicators that indicate a certain condition for each condition in the list of conditions. In some embodiments, rules 154 may include terms associated with the list of pre-defined conditions. For example, the term "pregnancy" may be associated with condition "maternity" in rules 154. Here, the term "pregnancy" can be considered an indicator for the condition "maternity." In some embodiments, each condition in the list of conditions in rules 154 can have own condition indicator set. In some embodiments, using rules 154 including the pre-defined conditions or the pre-defined condition indicators, tag generator 152 may generate NLP tags 170.

A machine learning model's inference quality may be evaluated manually to determine if the machine learning model needs further training. Embodiments of these technologies described can help improve machine learning model inferences using the quality metrics of inferences requested by a user. In some embodiments, the training happens based on predetermined rules, such as rules 154.

According to some embodiments of the present disclosure, recommendation engine 160 may include tag acquirer 161, parser 162, ranking module 163, and recommendation generating module 164. In some embodiments, recommendation engine 160 can also include mapping data 165. In some embodiments, mapping data 165 can be stored in a database, which may be fed data from an external source, or the external source (e.g., server, database, sensors, IoT devices, etc.) may be a replacement. In some embodiments, parser 162 may be configured to parse mapping data 165, which is described in detail in reference to FIG. 2A.

Figure 2A:
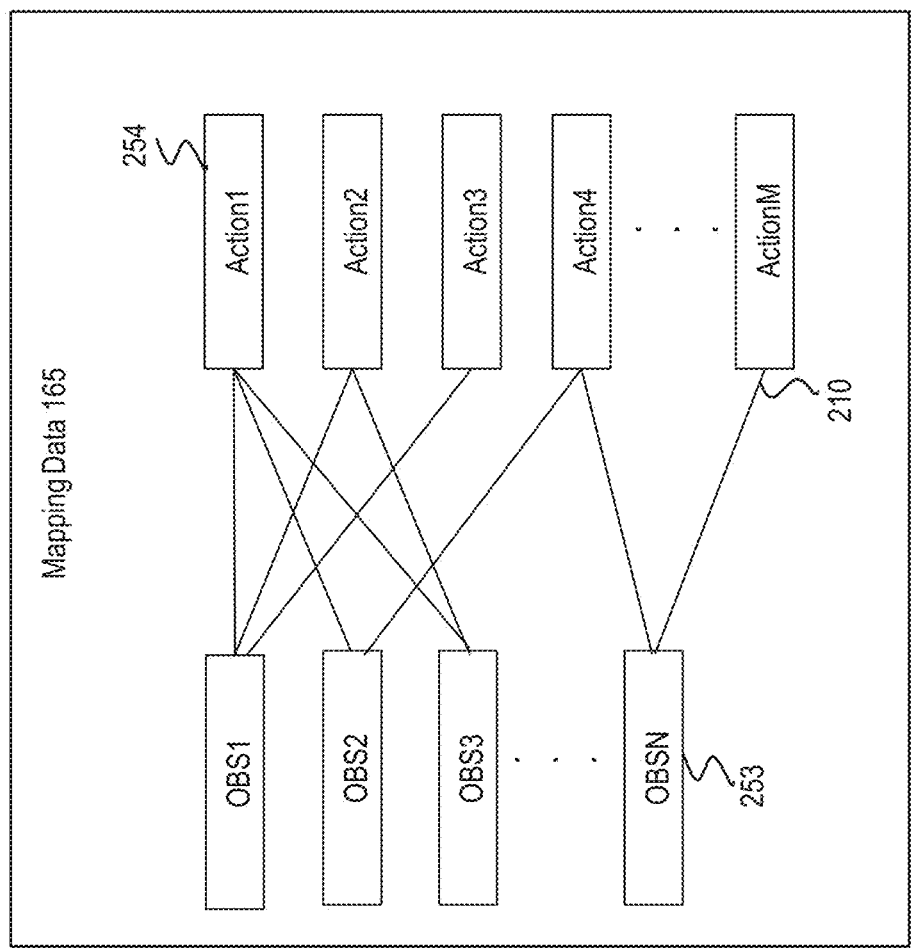
FIG. 2A is an exemplary structure of mapping data, according to some embodiments of the present disclosure.

FIG. 2A is an exemplary structure of mapping data, according to some embodiments of the present disclosure. In some embodiments, mapping data 165 may be stored in recommendation engine 160. In some embodiments, mapping data 165 can be generated based on historical data of a plurality of members. In some embodiments, recommendation system 100 can utilize historical data of a plurality of members after organizing the historical data as mapping data 165 as shown in FIG. 2A. As shown in FIG. 2A, mapping data 165 may associate observations 253 to actions 254. In some embodiments, observations may refer to a problem a member is experiencing. In a non-limiting example, an observation may be a healthcare problem associated with certain characteristics or symptoms. For example, an observation could be related to a diagnosis or condition, such as diabetes, or how a patient presents, such as pregnancy, based on the diagnosis or condition. Actions may refer to solutions that a provider provided for a certain observation. For example, in the case of a pregnancy observation, an action may refer to family planning services for a patient. In some embodiments, an observation may be mapped to a single action using an observation edge 210. In other embodiments, an observation may be mapped to multiple actions using observation edge 210.

For example, as shown in FIG. 2A, OBS1 is mapped to Action1, Action2, and Action3, which is indicated by three observation edges 210. OBS2 has two observation edges 210 mapped to Action1, and Action 4. OBS3 has two observation edges 210 mapped to Action1 and Action 2. FIG. 2A also illustrates that there may be N number of observations 253 and M number of actions 254. FIG. 2A is an exemplary embodiment of mapping data 165 for illustrative purposes only and indicates that the number of observations 253 and actions 254 is not necessarily limited to a certain number.

In some embodiments, mapping data 165 may comprise prior data for a plurality of members, including data related to previous observations, actions, etc. While FIG. 2A illustrates mapping data 165 include observations 253 and actions 254, it will be appreciated that mapping data 165 can further include benefits mapped to corresponding actions members have chosen for the corresponding actions in the historical data. Mapping data 165 may be generated based on all historical data for all members in recommendation system 100. While mapping data 165 is described to utilize edges 210 for associating observations with actions in FIG. 2A, it will be appreciated that mapping data 165 can be organized using any other mechanism for associating observations with corresponding actions, such as a table.

Figure 2B:
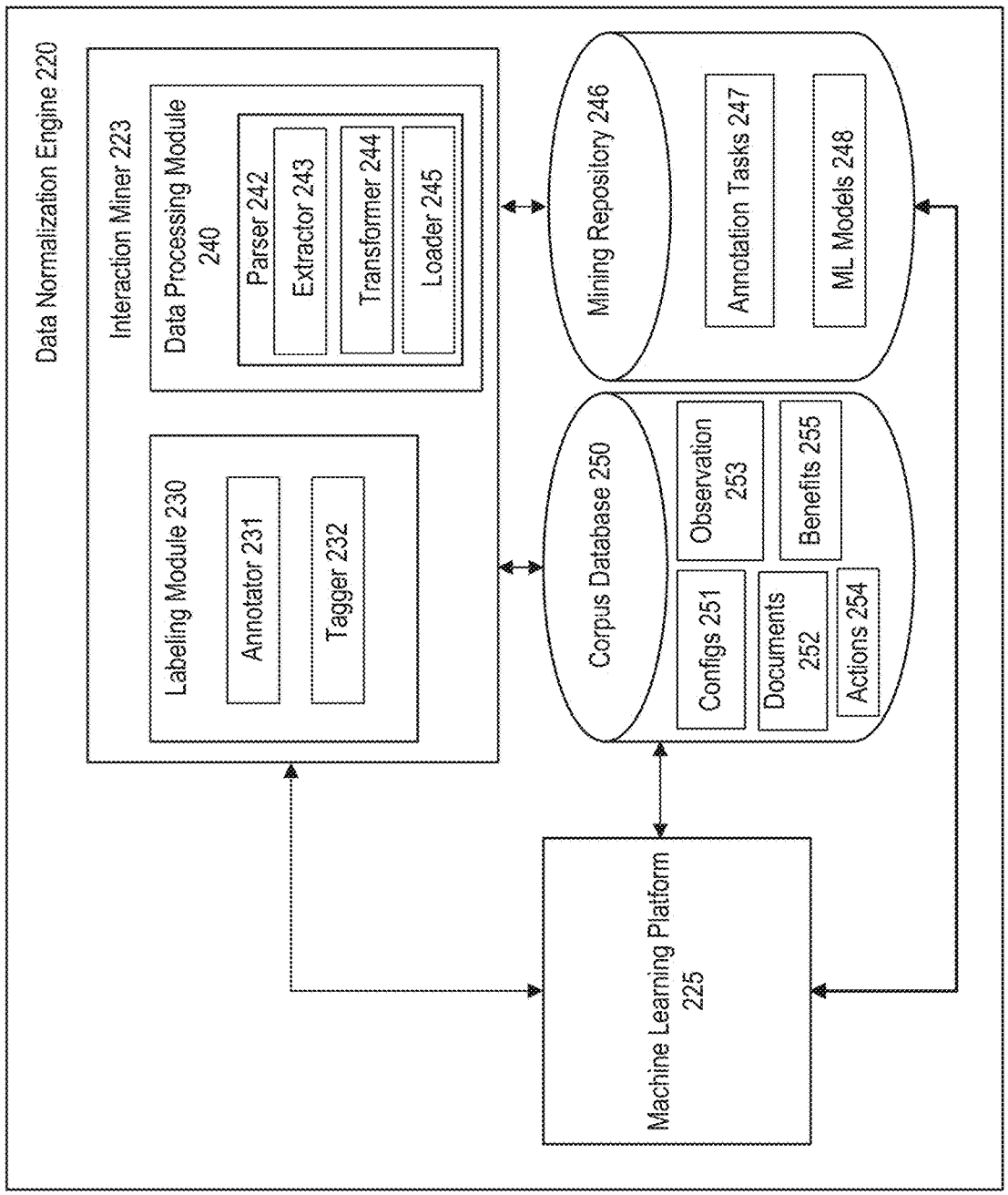
FIG. 2B is a block diagram illustrating various exemplary components of a data normalization engine, according to some embodiments of the present disclosure.

FIG. 2B is a block diagram illustrating various exemplary components of a data normalization engine 220 comprising natural language processing modules, according to some embodiments of the present disclosure. To organize historical data into mapping data 165, data normalization engine 220 may preprocess historical data, which can be from multiple data sources to perform data normalization. For instance, in a healthcare setting, data normalization engine 220 may normalize data pertaining to a patient's medical visit. Data normalization may comprise pre-processing historical data in different formats or historical data from different sources to generate mapping data 165. Pre-processing the historical data also helps with the ability to search the historical data quickly to provide a real-time recommendation. For example, recommendation system 100 can search relevant observations, actions, or benefits in real-time as NLP tags 170 are generated. Pre-processing the historical data may also improve accuracy and reliability of the data by removing missing or inconsistent data values resulting from human or computer error, thus improving the accuracy and quality of the historical data. This helps ensure the historical data more reliable and consistent when providing a real-time recommendation.

The historical data may be pre-processed to provide a real-time recommendation using data normalization engine 220. Pre-processing the historical data may comprise data cleaning to account for missing values, removing outliers, correcting inconsistent data points and smoothing noisy data. Pre-processing the data may further comprise data integration when historical data is collected from various sources. Integration may lead to inconsistent or redundant data points. Thus, integration may comprise consolidating the data to store it in one place to increase efficiency and productivity and to ensure there are no overlapping or inconsistent data points. Pre-processing historical data may also comprise data transformation, which may involve converting data from one format to another to ensure all data is in an appropriate format. In FIG. 2B, data normalization engine 220 may normalize data based on natural language processing modules, which can be similar to NLP engine 150 described with respect to FIG. 1. In some embodiments, natural language processing modules may include, but are not limited to, a labeling module 230, or a data processing module 240. Data normalization engine 220 may perform data normalization based on one or more corpus databases as exemplified by 250, or a mining repository as exemplified by mining repository 246.

Data normalization engine 220 may include interaction miner 223 to determine labels to associate with historical data of a plurality of members from multiple sources. Data normalization engine 220 may use additional configuration details. Interaction miner 223 may include labeling module 230 and data processing module 240 to determine labels. Interaction miner 223 may use corpus database 250 to store and access various labels of historical data. Interaction miner 223 may use mining repository 246 to get the definitions of tasks and models to generate labels. Interaction miner 223 works with machine learning model platform 225, corpus database 250, and mining repository 246 to generate labels and semi-supervised and unsupervised.

Data normalization engine 220 may also include Machine Learning (ML) platform 225 to help determine labels to associate with historical data. Interaction miner 223 and ML model platform 225 may access data and configurations in corpus database 250 and mining repository 246 to generate labels to determine insights.

Labeling module 230 may aid in labeling input data from historical data. Labeling module 230 may store parts of the retrieved input data along with generated labels in corpus database 250. Labeling module 230 may include manual processing of input data using annotator 231 and automatic and real-time processing of input data using tagger 232 to generate labels. In some embodiments, labeling module 230 may be configured to generate different labels and types of labels for matching data. Configurations may include configurations for annotator 231 and tagger 232 and stored in corpus database 250.

Annotator 231 may help annotate historical data by providing a list of annotations to use with the content in historical data. Annotator 231 may be configured to include the list of annotations to process with a list of annotators. Annotator 231 may receive a configuration (e.g., from a configuration file) over a network (not shown). The configuration file may be a text file or a structured document such as a YAML or JSON. In some embodiments, the configuration file may include a list of documents or a database query to select the list of documents. In some embodiments, a list of documents may be presented as a regex formula to match a set of documents. The configuration file may include additional details for annotations in mining repository 246.

Tagger 232 may automatically tag data with labels using machine learning (ML) model platform 225. Data Normalization Engine 220 may train tagger 232 using data annotated with labels provided by annotator 231. In some embodiments, tagger 232 may be used with unstructured data and need auto labeling of the data.

Data processing module 240 takes as input historical data and labels provided by annotator 231 and tagger 232 to generate insights about the contents of the input historical data. In some embodiments, insights may represent potential interactions between two or more labelled entities within the data. Data processing module 240 may store the insights in corpus database 250. Data processing module 240 may include aggregator 241 to help combine various interaction parts in the data to generate insights.

Parser 242 may retrieve data from various data sources and process the data to documents 252 so that it may be used with the remainder of data normalization engine 220. In some embodiments, parser 242 may parse the historical data from multiple sources and collect it in one place, such as mining repository 246. Parser 242 may further include extractor 243, transformer 244, and loader 245 modules. Extractor 243 and transformer 244 may work together to generate documents 252 and other data in corpus database 250. Transformer 244 may connect the disparate data extracted from multiple sources by extractor 243 and store it in corpus database 250.

Extractor 243 may retrieve historical input data from multiple sources, and each of these data sources may represent a different type of data source. For instance, in a healthcare setting, a data source may represent structured data such as hierarchical topics selected by a service provider communicating with a user or a usage log of a service by a user. In some embodiments, data sources may be flat files, such as call and chat transcripts. Further, data sources may contain overlapping or completely disparate data sets. In some embodiments, a data source may contain information about a user usage log of a service. In contrast, other data sources may contain various disparate topics a user discussed with a service provider. Extractor 243 may interact with various data sources, retrieve the relevant data, and provide that data to transformer 244.

Transformer 244 may receive data from extractor 243 and process the data into standard formats. In some embodiments, transformer 244 may normalize data such as dates. For example, a data source for a service usage log may store dates in a day-month-year format, while a data source for chat transcripts may store dates in a year-month-day format. In this example, transformer 244 may modify the data provided through extractor 243 into a consistent data format. Accordingly, transformer 244 may effectively clean the data provided through extractor 243 so that all of the data, although originating from a variety of sources, has a consistent format. For example, usage data may include a user ID of a user, but a chat transcript may include the full name of the same user. In the second example, transformer 244 may include the missing full name in a usage log of a service.

Moreover, transformer 244 may extract additional data points from the data sent by extractor 243. For example, transformer 244 may process a date in a year-month-day format by extracting separate data fields for the year, the month, and the day. Transformer 244 may also perform other linear and non-linear transformations and extractions on categorical and numerical data, such as normalization and demeaning. Transformer 244 may provide the transformed or extracted data to loader 245. In some embodiments, transformer 244 may store the transformed data in corpus database 250 for later use by loader 245 and other components of interaction miner 223.

Loader 245 may receive normalized data from transformer 244. Loader 245 may merge the data into varying formats depending on the specific requirements of data normalization engine 220 and store the data in an appropriate storage mechanism such as corpus database 250. Loader 245 may store input data processed by various components of parser 242 as documents 252.

Corpus database 250 may include raw input data stored as documents 252 and configurations to label documents as configs 251. Configs 251 may include configuration parameters to determine labels to associate with documents 252 and generate insights of interaction content in documents 252. Configs 251 may include a configuration file sent over a network. Configs 251 may include flat files in an unstructured format as text files or semi-structured XML or JSON files. In some embodiments, configs 251 may include parsed content from a configuration file. Configs 251 may store parsed content as database tables.

Corpus database 250 may also contain observations 253, actions 254, and benefits 255. Observations 253 may be specialized labels associated with documents 252 to indicate the problems of users interacting with service providers. Observations 253 may include links with documents 252. Tagger 232 may use a different ML model of ML models 248 to associate observations of observations 253 with corresponding documents in documents 252. Actions 254 may be specialized labels associated with documents 252 to indicate the solutions provided by service providers interacting with users. Actions 254 may include links with documents 252. Tagger 232 may use a different ML model of ML models 248 to associate actions of actions 254 with corresponding documents in documents 252. Benefits 255 may be specialized labels associated with documents 252 to indicate the services that users selected from service providers for the solutions. Benefits 255 may include links with documents 252. Tagger 232 may use a different ML model of ML models 248 to associate benefits of benefits 255 with corresponding documents in documents 252.

Mining repository 246 may include various configurations and definitions for extracting relevant parts from input data to store in corpus database 250. Mining repository 246 may include annotation tasks 247 and ML models 248 to define and assign labels to content in documents 252.

Annotation tasks 247 include definitions of annotations to add as labels to documents 252. A user of data normalization engine 220 may provide definitions of annotations as part of a configuration file (e.g., configs 251).

ML Models 248 may include machine learning models trained by interaction miner 223 using ML model platform 225. ML models 248 may be trained using training data in corpus database 250. ML models 248 may be configured using configs 251 and set up for training using annotation tasks 247. Annotations identified using annotation tasks 247 may be used as training data for ML models 248.

In various embodiments, corpus database 250, mining repository 246, and historical data may take several different forms. For example, mining repository 246 may be an SQL or NoSQL database, such as those developed by MICROSOFT™, REDIS, ORACLE™ CASSANDRA, MYSQL, various other types of databases, data returned by calling a web service, data returned by calling a computational function, sensor data, IoT devices, or various other data sources. Corpus database 250 may store data that is used during the operation of applications, such as interaction miner 223. In some embodiments, corpus database 250 and mining repository 246 may be fed data from an external source, or the external source (e.g., server, database, sensors, IoT devices, etc.) may be a replacement. In some embodiments, corpus database 250 may be data storage for a distributed data processing system (e.g., Hadoop Distributed File System, Google File System, ClusterFS, or OneFS). Depending on the specific embodiment of corpus database 250, interaction miner 223 may optimize the label data for storing and retrieving in corpus database 250 for optimal query performance.

Referring back to FIG. 1, according to some embodiments of the present disclosure, tag acquirer 161 can be configured to acquire NLP tags 170 from tag generator 152. In some embodiments, NLP tags 170 can be forwarded to tag acquirer 161 as NLP tags 170 are generated by tag generator 152.

According to some embodiments, parser 162 may parse mapping data 165 based on the received NLP tag 170. In some embodiments, parser 162 parses mapping data 165 to generate a list of actions 254 related to the acquired NLP tags 170. In some embodiments, parser 162 may first extract observations 253 related to NLP tags 170. After parser 162 extracts observations 253, parser 162 may extract actions 254 based on observations 253. The parsing process is described with reference to FIG. 3A, which is an exemplary flow diagram for providing recommendation(s), according to some embodiments of the present disclosure. FIG. 3A illustrates one NLP tag 170 is generated by NLP engine 150, such as clinical_diabetes. As shown in FIG. 3A, parser 162 has extracted one observation OBS1 to be related to the generated NLP tag 170 from mapping data 165, e.g., shown in FIG. 2A. For example, observation OBS1 can be a symptom (e.g., diabetic complications) the user suffers from the condition diabetes. FIG. 3A further illustrates that parser 162 has extracted three actions to be related to the generated NLP tag 170 from mapping data 165, e.g., shown in FIG. 2A. Because observation OBS1, which is determined to be related to the generated NLP tag 170, is mapped to three actions Action1, Action2, and Action3 in mapping data 165, parser 162 can extract three actions Action1-Action3 as being related to the generated NLP tag 170 from mapping data 165. For example, one of the extracted actions can be a treatment to diabetic complications.

Referring back to FIG. 1, ranking module 163 may rank actions extracted from parser 162 based on preconfigured rules. According to some embodiments of the present disclosure, ranking of extracted actions can be determined based on mapping data 165. As an example, FIG. 3A illustrates that three actions Action1 to Action3 are extracted from mapping data based on relevancy to the generated NLP tag 170. When ranking the extracted actions, ranking module 163 can consider the number of observations mapped to a certain action in mapping data 165. In some embodiments, an action having the less number of observations mapped thereto can have the higher ranking. In FIG. 2A, it is shown that Action1 is mapped to three observations OBS1, OBS2, and OBS3, Action2 is mapped to two observations OBS1 and OBS3, and Action3 is mapped to one observation OBS3. In this example, Action3 has the highest ranking (i.e., the first place) as Action3 has the least number of observations mapped to Action3. And Action2 takes the second place and Action1 takes the third place. By ranking an action with a less number of mapped observations to have a higher ranking, actions that are more specific to a certain observation can have a higher ranking than actions that are generally applied to various observations.

Referring back to FIG. 1, according to some embodiments, recommendation generating module 164 is configured to generate recommendation(s) based on the ranked actions. In some embodiments, recommendation generating module 164 can generate one or more benefits 255 that are determined to be related to the ranked actions. In some embodiments, recommendation generating module 164 can select benefits 255 among a list of benefits available to a particular member associated with the generated NLP tags 170.

In FIG. 3A, it is shown that two benefits 255, i.e., Benefit1 and Benefit2 are determined to be relevant to ranked actions Action1, Action2, and Action3. In some embodiments, recommendation generating module 164 can provide the generated benefits 255 as a service recommendation. In some embodiments, when there is more than one benefit 255 to be provided as service recommendation, benefits can also be ranked. In some embodiments, benefits can be ranked based on the average rank for the actions linked to the corresponding benefit. For example, in FIG. 3A, Benefit1 is linked to Action1 and Action2. And the average rank of Action1 and Action2 is 2.5 as Action1 is ranked third and Action2 is ranked second. Similarly, Benefit2 is linked to Action2 and Action3, and the average rank of Action2 and Action3 is 1.5. In this example, Benefit2 can be ranked higher than Benefit1. In some embodiments, recommendation generating module 164 may provide only one benefit having the highest ranking. In some other embodiments, recommendation generating module 164 may provide multiple benefits based on the ranking. For example, Benefit2 can be provided as a first recommendation and Benefit1 can be provided as a second recommendation. In some embodiments, recommendation generating module 164 can provide benefits only related to a certain number of actions from the highest ranking. For example, recommendation generating module 164 can provide benefits only related to the highest ranked action. In the example of FIG. 3A, only Benefit2 is linked to Action3, which is ranked first, and thus Benefit2 can be provided as a service recommendation. When recommending benefits, recommendation generating module 164 may only generate benefits 255 that can be applied to a particular member. Benefits 255 may be related to member care, including insurance benefits, treatment benefits, and care benefits. In some embodiments, recommendation system 100 can provide generated Benefits 255 as service recommendation to display to user 122 on user interface 124.

According to some embodiments where mapping data 165, e.g., shown in FIG. 2A, include benefits 255, parser 162 can further be configured to extract benefits 255 related to the generated NLP tags 170. In this scenario, ranking module 163 can further be configured to rank the extracted benefits based on the ranked actions as discussed above, and recommendation generating module 164 can provide one or more benefits as service recommendation based on the ranked benefits.

While some embodiments where one NLP tag 170 is generated have been described referring to FIG. 3A, it will be appreciated that the present disclosure can be applied to any number of NLP tags. FIG. 3B is another exemplary flow diagram for providing recommendation(s), according to some embodiments of the present disclosure. FIG. 3B illustrates two NLP tags 170 are generated by NLP engine 150, such as clinical_diabetes and clinical_maternity. In some embodiments, NLP tags 170 may not be related to one another and a member may have multiple health issues. As shown in FIG. 3B, parser 162 has extracted three observations OBS1, OBS2, and OBS3 to be related to the generated NLP tags 170 from mapping data 165, e.g., shown in FIG. 2A. For example, observation OBS1 can be related to NLP tag clinical_diabetes and observations OBS2 and OBS3 can be related to NLP tag clinical_maternity. FIG. 3B further illustrates that parser 162 has extracted four actions to be related to the generated NLP tags 170 from mapping data 165. Because observations OBS1, OBS2, and OBS3 are mapped to four actions Action1, Action2, Action3, and Action4 in mapping data 165, parser 162 can extract four actions Action1-Action4 as being related to the generated NLP tags 170 from mapping data 165.

In ranking module 163, the extracted actions may be ranked. In FIG. 3B, four actions, Action1 to Action4 are extracted from mapping data 165 to be relevant to the generated NLP tags 170. When ranking the extracted actions, ranking module 163 can consider the number of observations mapped to a certain action in mapping data 165. In some embodiments, an action having the least number of observations mapped thereto may have the higher ranking. In FIG. 2A, it is shown that Action1 is mapped to three observations OBS1, OBS2, and OBS3, Action2 is mapped to two observations OBS1 and OBS3, Action3 is mapped to one observation OBS3, and Action4 is mapped to two observation OBS2 and OBSN. In this example, Action3 has the highest ranking (i.e., the first place) as Action3 has the least number of observations mapped to Action3. Action2 and Action4 are tied for second place and Action1 takes fourth place.

Recommendation generating module 164 may generate a list of benefits 255 that are determined to be related to the ranked actions. As shown in FIG. 3B, three benefits 255, i.e., Benefit1, Benefit2, and Benefit3 are determined to be relevant to ranked actions Action1, Action2, Action3, and Action4. In some embodiments, recommendation generating module 164 may provide the generated benefits 255 as a service recommendation. In FIG. 3B, Benefit1 is linked to Action1 and Action2, Benefit2 is linked to Action2, and Benefit3 is linked to Action3 and Action4. The average rank of Action1 and Action2 is 3 as Action1 is ranked fourth and Action2 is ranked second. Similarly, Benefit2 is linked to Action2 and Action3, and the average rank of Action2 and Action3 is 2. Benefit3 is linked to Action3 and Action4, and the average rank of Action3 and Action 4 is 1.5. In this example, Benefit3 may be ranked higher than Benefit2, and Benefit2 maybe ranked higher than Benefit1. Thus, Benefit3 maybe provided as a first recommendation, Benefit2 may be a second recommendation, and Benefit1 may be a last recommendation. As discussed in reference to FIG. 3A, in some embodiments, recommendation generating module 164 may provide benefits only related to a certain number of actions from the highest ranking. For example, recommendation generating module 164 may provide benefits only related to the highest ranked action. In the example of FIG. 3B, only Benefit3 is linked to Action3, which is ranked first, and thus Benefit3 may be provided as a service recommendation.

Figure 4:
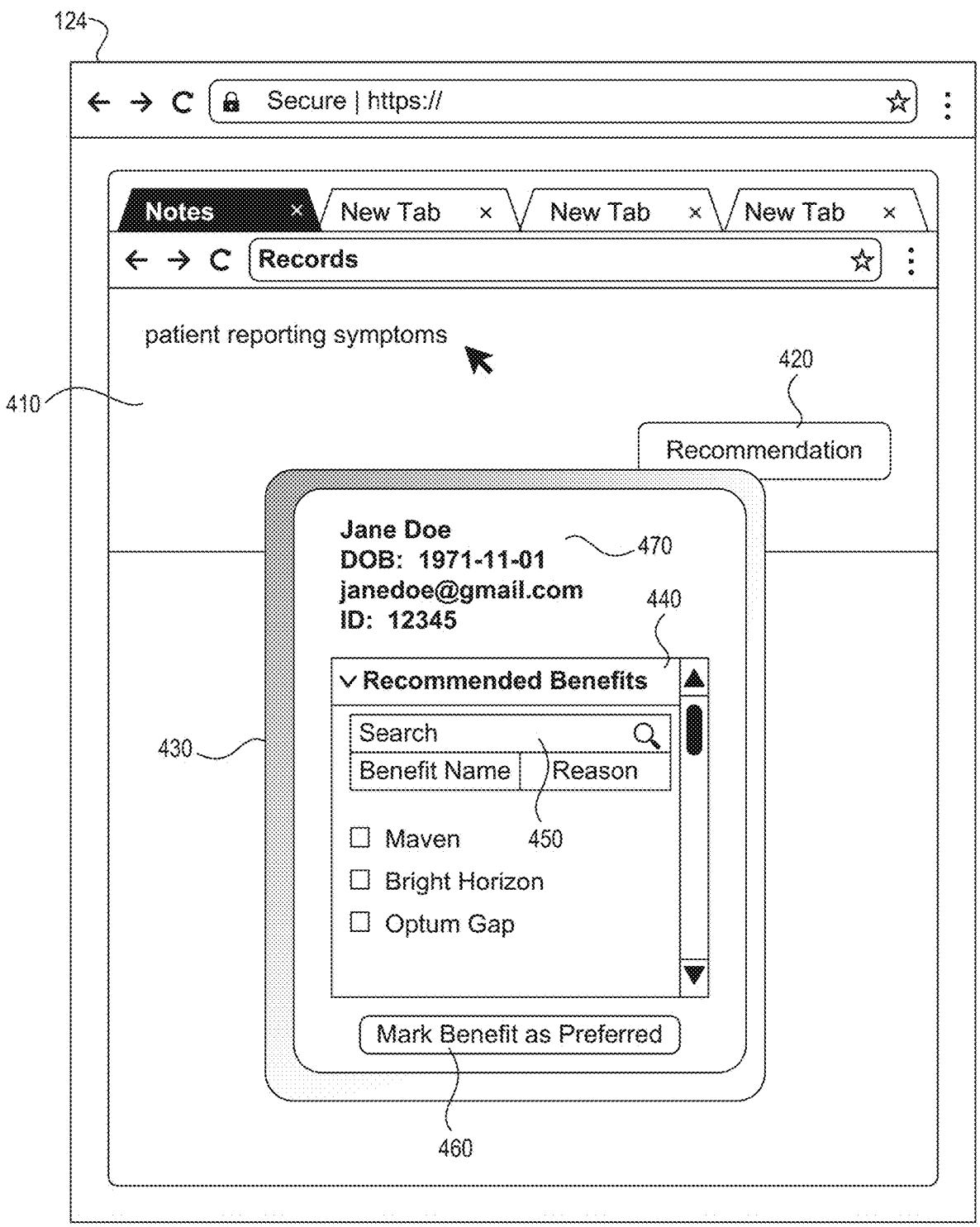
FIG. 4 is an exemplary user interface diagram, according to some embodiments of the present disclosure.

FIG. 4 is an exemplary user interface diagram, according to some embodiments of the present disclosure. As shown in FIG. 4, user interface 124 may include note field 410 and recommendation request icon 420. In FIG. 4, user interface 124 may further include recommendation pop-out window 430 that may display recommended benefits 440, search function 450, preferred benefit marker 460, member data 470, etc. In some embodiments, user interface 124 may appear if browser plug-in 130 is installed.

In some embodiments, note field 410 may be a section where user 122 takes notes. In note field 410, user 122 can take notes related to current symptoms, the severity of symptoms, medical history, current medications, health related issues, feelings, etc. In note field 410, physical findings may be recorded, which are gathered from seeing a member such as vital signs, member appearance, behavior, and mood, and other relevant medical records or information. In note field 410, user 122 can also take notes related to an assessment of the member based on the provider's impressions and interpretations. In note field 410, user 122 can also record a plan for member treatment and an assessment.

Recommendation request icon 420 may be an exemplary clickable button that user 122 may select for recommendation pop-out window 430 to appear. Recommendation pop-out window 430 may be another user interface that appears once recommendation request icon 420 is selected. According to some embodiments of the present disclosure, recommendation pop-out window 430 comprising recommended benefits 440 may be provided in real-time in response to a recommendation request, e.g., via recommendation request icon 420. Recommendation pop-out window 430 may comprise recommended benefits 440, search function 450, preferred benefit marker 460, and member data 470.

In some embodiments, recommended benefits 440 comprises a comprehensive list of recommended benefits based on note field 410, using recommendation engine 160 as described with respect to FIG. 1.

In some embodiments, user 122 may select preferred benefit marker 460 to indicate that among the list of recommended benefits 440, a preferred benefit. A member may see both the list of recommended benefits 440 and the preferred benefits.

In some embodiments, search function 450 may be used by user 122 to search for a particular benefit. In some embodiments, user 122 may search benefits by a benefit name.

In some embodiments, member data 470 may comprise member information such as a name, date of birth, e-mail address, and a unique member identifier.

Figure 5:
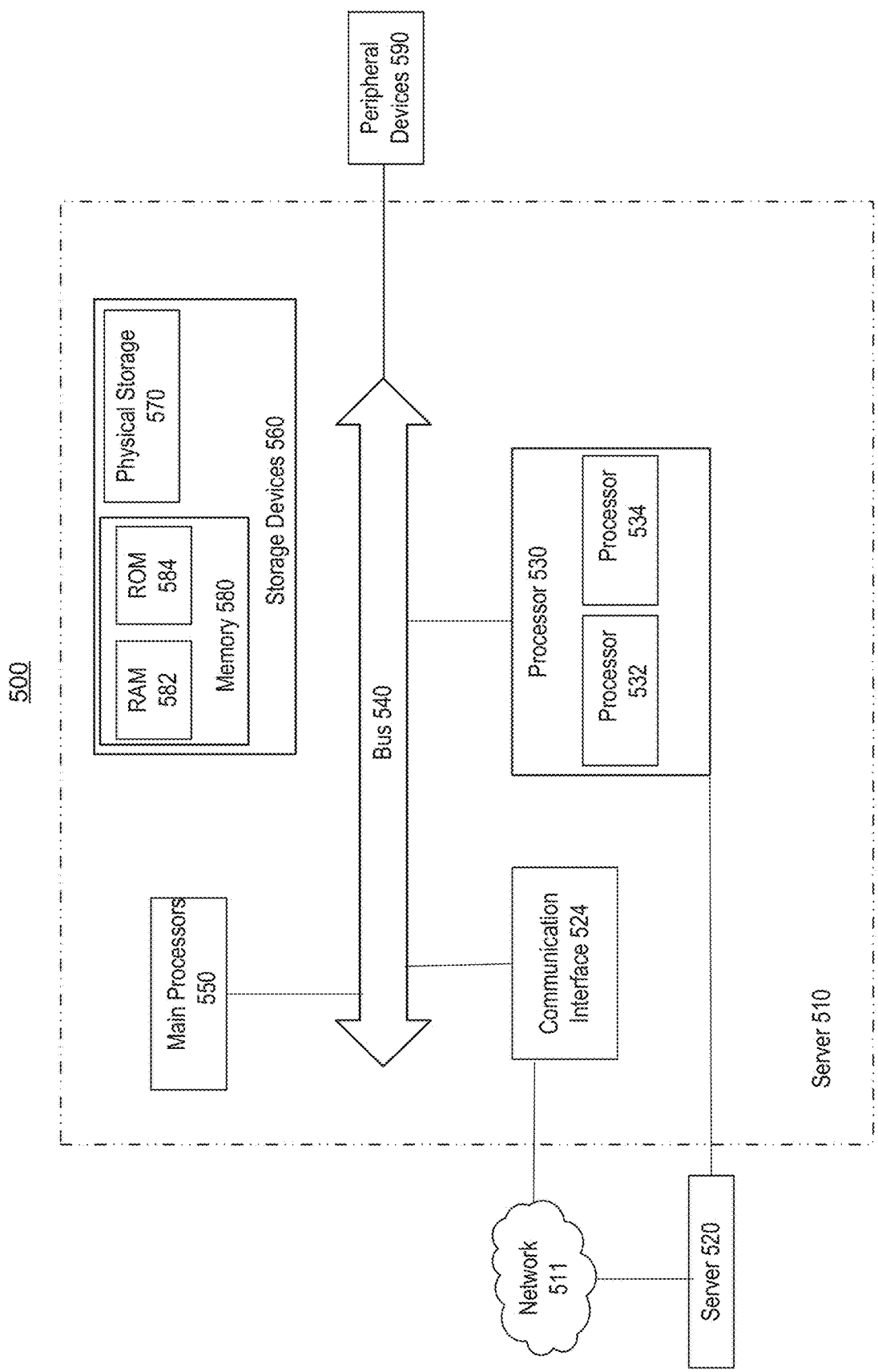
FIG. 5 illustrates a schematic diagram of an exemplary server of a distributed system, according to some embodiments of the present disclosure.

FIG. 5 illustrates a schematic diagram of an exemplary server of a distributed system, according to some embodiments of the present disclosure. According to FIG. 5, server 510 of distributed computing system 500 comprises a bus 540 or other communication mechanisms for communicating information, one or more processors 530 communicatively coupled with bus 540 for processing information, and one or more main processors 550 communicatively coupled with bus 540 for processing information. Processors 530 can be, for example, one or more microprocessors. In some embodiments, one or more processors 530 comprises processor 532 and processor 534, and processor 532 and processor 534 are connected via an inter-chip interconnect of an interconnect topology. In some embodiments, processor 534 can be a dedicated hardware accelerator (such as a neural network processing unit) for processor 532. Main processors 550 can be, for example, central processing units ("CPUs").

Server 510 may transmit data to or communicate with another server 520 through a network 511. Network 511 may be a local network, an internet service provider, Internet, or any combination thereof. Communication interface 524 of server 510 is connected to network 511, which may enable communication with server 520. In addition, server 510 can be coupled via bus 540 to peripheral devices 590, which comprises displays (e.g., cathode ray tube (CRT), liquid crystal display (LCD), touch screen, etc.) and input devices (e.g., keyboard, mouse, soft keypad, etc.).

Server 510 may be implemented using customized hard-wired logic, one or more ASICs or FPGAs, firmware, or program logic that in combination with the server causes server 510 to be a special-purpose machine.

Server 510 further comprises storage devices 560, which may include memory 580 and physical storage 570 (e.g., hard drive, solid-state drive, etc.). Memory 580 may include random access memory (RAM) 582 and read-only memory (ROM) 584. Storage devices 560 maybe communicatively coupled with processors 530 and main processors 550 via bus 540. Storage devices 560 may include a main memory, which can be used for storing temporary variables or other intermediate information during execution of instructions to be executed by processors 530 and main processors 550. Such instructions, after being stored in non-transitory storage media accessible to processors 530 and main processors 550, render server 510 into a special-purpose machine that is customized to perform operations specified in the instructions. The term "non-transitory media" as used herein refers to any non-transitory media storing data or instructions that cause a machine to operate in a specific fashion. Such non-transitory media can comprise non-volatile media or volatile media. Non-transitory media include, for example, optical or magnetic disks, dynamic memory, a floppy disk, a flexible disk, hard disk, solid state drive, magnetic tape, or any other magnetic data storage medium, a CD-ROM, any other optical data storage medium, any physical medium with patterns of holes, a RAM, a PROM, and an EPROM, a FLASH-EPROM, NVRAM, flash memory, register, cache, any other memory chip or cartridge, and networked versions of the same.

Various forms of media can be involved in carrying one or more sequences of one or more instructions to processors 530 or main processors 550 for execution. For example, the instructions can initially be carried out on a magnetic disk or solid-state drive of a remote computer. The remote computer can load the instructions into its dynamic memory and send the instructions over a telephone line using a modem. A modem local to server 510 can receive the data on the telephone line and use an infra-red transmitter to convert the data to an infra-red signal. An infra-red detector can receive the data carried in the infra-red signal, and appropriate circuitry can place the data on bus 540. Bus 540 carries the data to the main memory within storage devices 560, from which processors 530 or main processors 550 retrieves and executes the instructions.

Recommendation system 100 (as shown in FIG. 1) or one or more of its components may reside on either server 510 or 520 and may be executed by processors 530 or 550. In some embodiments, the components of recommendation system 100 may be spread across multiple servers 520 and 510. Similarly, data normalization engine 220 (as shown in FIG. 2B) or one or more its components may reside on either 510 or 520 and may be executed by processors 530 or 550.

User device 120 may communicate with server 510 or 520 through network 110. For example, user device 120 may transmit activity of user 122 to server 510 or 520. Server 510 or 520 may include any form of remote computing device configured to receive, store, and transmit data. For example, server 510 or 520 may be a server configured to store files accessible through a network (e.g., a web server, application server, virtualized server, etc.). Server 510 or 520 may be implemented as a Software as a Service (SaaS) platform through which software for auditing recorded user activity may be provided to an organization as a web-based service.

Figure 6:
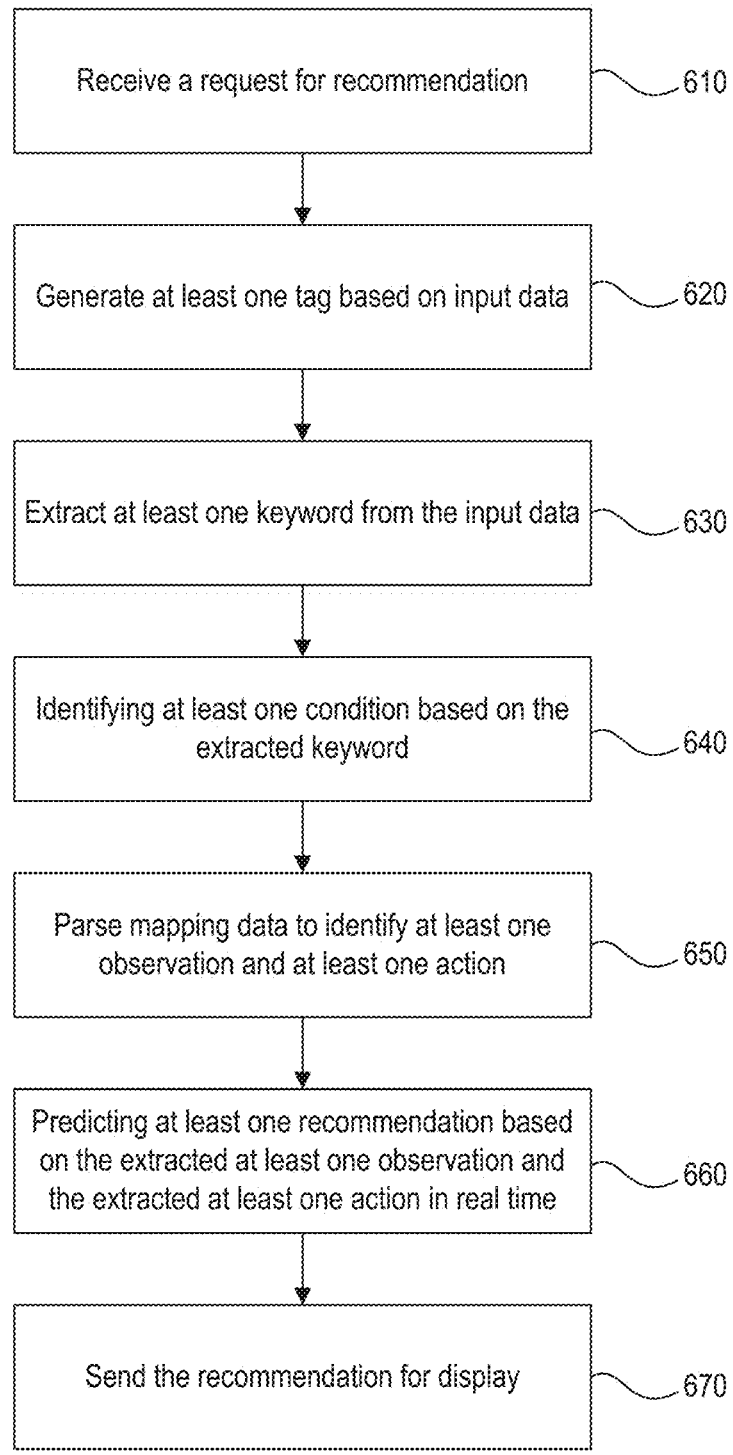
FIG. 6 is a flowchart showing an exemplary method for providing a real-time recommendation, according to some embodiments of the present disclosure.

FIG. 6 is a flowchart showing an exemplary method for providing a real-time recommendation, according to some embodiments of the present disclosure. The steps of method 600 may be performed by, for example, recommendation system 100 of FIG. 1. It is appreciated that the illustrated method 600 may be altered to modify the order of steps and to include additional steps.

In step 610, recommendation system 100 may receive a request for a service recommendation. In some embodiments, the request may be made by a service provider over a network, such as network 110 using a browser plug-in, such as browser plug-in 130, as described with respect to FIG. 1.

In step 620, recommendation system 100 may generate at least one tag based on input data. Input data may be input data 132, as described with respect to FIG. 1. Input data may be pre-processed by preprocessing module 151 as described with respect to FIG. 1. In some embodiments, the data may be received through a browser plug-in, such as browser plug-in 130, through request acquirer 140, as described with respect to FIG. 1. In some embodiments, browser plug-in 130 may send historical data to natural language processing engine 150 and recommendation engine 160. In some embodiments of the data may be acquired through previously retrieved data stored in a database. In some embodiments, recommendation system 100 may retrieve data in real-time when a user communicates with a service provider through email, chat message, or phone call. In some embodiments, the generated tag may be an NLP tag, such as NLP tag 170, as described with respect to FIG. 1. In some embodiments, processing may occur using a natural language processing engine, such as natural language processing engine 150, as described in FIG. 1. In some embodiments, natural language processing engine may use a machine learning platform to generate tags, such as machine learning platform 153, as described in FIG. 1.

In step 630, recommendation system 100 may extract at least one keyword from the input data. In some embodiments, keyword extract may comprise extracting the most used and most important words from input data 132. In some embodiments, keyword extraction may be performed by tag generator 152, as described in FIG. 1. In some embodiments, keyword extraction may comprise extracting keywords from recognized text in input data 132.

In step 640, recommendation system may identify at least one condition based on the extracted at least one keyword. In some embodiments, the identified conditions may be generated as NLP tags, such as NLP tags 170, as described with respect to FIG. 3A and FIG. 3B.

In step 650, recommendation system 100 may parse mapping data to identify at least one observation and at least one action based on the at least one condition identified in step 640. In some embodiments, mapping data may associate observations to actions, as shown in FIG. 2A. In some embodiments, mapping data may comprise prior data for a plurality of members, including data related to previous observations, actions, etc, while input data is related to a particular, individual member. Mapping data may be generated based on all historical data for all members in recommendation system 100.

In some embodiments, parsing may occur using parser 162 to parse mapping data, such as mapping data 165, as described with respect to FIG. 1 and FIG. 2A. As described previously, in a non-limiting example, an observation may be a healthcare problem associated with certain characteristics or symptoms and may be an observation such as observations 253, as described in FIG. 2B. Actions may refer to solutions that a provider may provide for a certain observation, such as actions 254 as described in FIG. 2B. In some embodiments parsing may comprise browsing the historical data and extracting certain phrases or words using natural language processing techniques to identify certain key words, such as people, objects, concepts, or observations. In some embodiments, parser 162 may first extract observations 253 related to NLP tags 170. After parser 162 extracts observations 253, parser 162 may extract actions 254 based on observations 253.

In step 660, recommendation system 100 may predict at least one recommendation based on the extracted at least one observation and the extracted at least one action in real time. In some embodiments, the predicting may further comprise determining a number of observation edges 210 associated with at least one action 254. In a non-limiting example, an action may be associated with a benefit recommendation in a healthcare environment. The observations 253 may be mapped mapped to particular actions 254 using observation edges 210, as illustrated in FIG. 2A. In some embodiments, the action with the least number of observation edges 210 may be selected to determine a benefit recommendation. The level of specificity of an observation edges 210 associated with an action may determine which recommendation system 100 generates. In some embodiments, the number of observation edges 210 is mapped to the received user information. In some embodiments, the at least one action is ranked based on the observation edges 210 to determine the at least one recommendation. In some embodiments, the ranking is based on the number of observation edges 210 mapped to the at least one action 254. In some embodiments, the ranking further comprises ranking the at least one action with the least amount of observation edges 210 as the highest. In some embodiments, the predicting is based on pre-configured rules. In some embodiments, rules can be added to the natural language processing engine 150 to improve the accuracy of the system. In some embodiments, natural language processing engine 150 may include multiple machine learning models to understand the historical data. Natural language processing engine 150 may choose the machine learning models based on user defined rules. Natural language processing engine 150 may use a model that identifies the core topics of each piece of historical data. For example, in a healthcare environment, the core topics may include clinical topics. Within the healthcare environment, a communication between a member and a provider may relate to a clinical discussion related to recommendations for an ailment or a referral to another provider specializing in an ailment. Natural language processing engine 150 may parse the historical data multiple times to retrieve the relevant information.

In step 670, recommendation system 100 may send the at least one predicted recommendation for display to a user device. In a non-limiting example, the real-time recommendation may be a benefit recommendation related to healthcare services. For example, in a healthcare environment, a benefit recommendation may include information about a specific diabetes benefit based on responses from a member and notes from a provider. Recommendation system 100 may send the at least one predicted recommendation for display to a user device in real-time, such as user device 120, as described with respect to FIG. 5. The user device may include any form of computer-based device or entity through which a member may access a navigation location. For example, the user device may be a personal computer (e.g., a desktop or laptop computer), a mobile device (e.g., a mobile phone or tablet), a wearable device (e.g., a smart watch, smart jewelry, implantable device, fitness tracker, smart clothing, head-mounted display, etc.), an IoT device (e.g., smart home devices, industrial devices, etc.), or any other device that may be capable of accessing web pages or other network locations. In some embodiments, the user device may be a virtual machine (e.g., based on AWS™, Azure™, IBM Cloud™, etc.), container instance (e.g., Docker™ container, Java™ container, Windows Server™ container, etc.), or other virtualized instance.

As used herein, unless specifically stated otherwise, the term "or" encompasses all possible combinations, except where infeasible. For example, if it is stated that a component may include A or B, then, unless specifically stated otherwise or infeasible, the component may include A, or B, or A and B. As a second example, if it is stated that a component may include A, B, or C, then, unless specifically stated otherwise or infeasible, the component may include A, or B, or C, or A and B, or A and C, or B and C, or A and B and C.

Example embodiments are described above with reference to flowchart illustrations or block diagrams of methods, apparatus (systems) and computer program products. It will be understood that each block of the flowchart illustrations or block diagrams, and combinations of blocks in the flowchart illustrations or block diagrams, can be implemented by computer program product or instructions on a computer program product. These computer program instructions may be provided to a processor of a computer, or other programmable data processing apparatus to produce a machine, such that the instructions, which execute via the processor of the computer or other programmable data processing apparatus, create means for implementing the functions/acts specified in the flowchart or block diagram block or blocks.

These computer program instructions may also be stored in a computer readable medium that can direct one or more hardware processors of a computer, other programmable data processing apparatus, or other devices to function in a particular manner, such that the instructions stored in the computer readable medium form an article of manufacture including instructions that implement the function/act specified in the flowchart or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions that execute on the computer or other programmable apparatus provide processes for implementing the functions/acts specified in the flowchart or block diagram block or blocks.

Any combination of one or more computer readable medium(s) may be utilized. The computer readable medium may be a non-transitory computer readable storage medium. In the context of this document, a computer readable storage medium may be any tangible medium that can contain or store a program for use by or in connection with an instruction execution system, apparatus, or device.

Program code embodied on a computer readable medium may be transmitted using any appropriate medium, including but not limited to wireless, wireline, optical fiber cable, RF, IR, etc., or any suitable combination of the foregoing.

Computer program code for carrying out operations, for example, embodiments may be written in any combination of one or more programming languages, including an objectoriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The flowchart and block diagrams in the figures illustrate examples of the architecture, functionality, and operation of possible implementations of systems, methods, and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts, or combinations of special purpose hardware and computer instructions.

It is understood that the described embodiments are not mutually exclusive, and elements, components, materials, or steps described in connection with one example embodiment may be combined with, or eliminated from, other embodiments in suitable ways to accomplish desired design objectives.

In the foregoing specification, embodiments have been described with reference to numerous specific details that can vary from implementation to implementation. Certain adaptations and modifications of the described embodiments can be made. Other embodiments can be apparent to those skilled in the art from consideration of the specification and practice of the invention disclosed herein. It is intended that the specification and examples be considered as exemplary only. It is also intended that the sequence of steps shown in figures are only for illustrative purposes and are not intended to be limited to any particular sequence of steps. As such, those skilled in the art can appreciate that these steps can be performed in a different order while implementing the same method.

What is claimed is:

1. A system for generating a real-time recommendation, comprising:
   one or more memory devices storing processor-executable instructions; and
   one or more processors configured to execute instructions to cause the system to perform operations comprising:
      receiving a request for a benefit recommendation;
      generating at least one tag based on input data associated with the received request and based on predefined rules that are associated with a list of pre-defined conditions;
      extracting at least one keyword from the input data using the at least one generated tag;
      identifying, based on the at least one extracted keyword, at least one condition corresponding to the list of pre-defined conditions;
      parsing mapping data to identify at least one observation and at least one action based on the at least one identified condition, wherein the mapping data associates observations with actions;
      predicting at least one recommendation based on the identified at least one observation and the identified at least one action in real time; and
      providing the at least one predicted recommendation for display to a user device, wherein the at least one predicted recommendation includes a preferred recommendation.

2. The system of claim 1, wherein the request is made by a service provider.

3. The system of claim 1, wherein predicting at least one recommendation further comprises:
   determining a number of observation edges associated with at least one action; and
   mapping the number of observation edges to a list of benefits.

4. The system of claim 3, wherein the operations further comprise ranking the at least one action based on the observation edges to determine the at least one recommendation.

5. The system of claim 4, wherein ranking the at least one action further comprises ranking the at least one action with the least amount of observation edges as the highest action.

6. The system of claim 4, wherein ranking the at least one action further comprises using the mapping data based on the at least one observation and the at least one action to determine a recommendation.

7. The system of claim 1, wherein generating at least one tag further comprises using a natural language processing engine.

8. The system of claim 7, wherein the natural processing engine uses a machine learning platform to generate tags.

9. The system of claim 1, further comprising a browser plugin to receive the request for a recommendation.

10. The system of claim 1, wherein predicting at least one recommendation is based on pre-configured rules.

11. A computer-implemented method for generating a real-time recommendation, comprising:
    receiving a request for a benefit recommendation;
    generating at least one tag based on input data associated with the receiving request and based on predefined rules that are associated with a list of pre-defined conditions;
    extracting at least one keyword from the input data using the at least one generated tag;
    identifying, based on the at least one extracted keyword, at least one condition corresponding to the list of pre-defined conditions;
    parsing mapping data to identify at least one observation and at least one action based on the identified at least one condition, wherein the mapping data associates observations with actions;
    predicting at least one recommendation based on the identified at least one observation and the identified at least one action in real time; and
    providing the at least one predicted recommendation for display to a user device, wherein the at least one predicted recommendation includes a preferred recommendation.

12. The method of claim 11, wherein the request is made by a service provider.

13. The method of claim 11, wherein the predicting further comprises:
   determining a number of observation edges associated with at least one action; and
   mapping the number of observation edges to a list of benefits.

14. The method of claim 13, further comprising ranking the at least one action based on the observation edges to determine the at least one recommendation.

15. The method of claim 14, wherein the ranking further comprises ranking the at least one action with the least amount of observation edges as the highest.

16. The method of claim 14, wherein the ranking further comprises using the mapping data based on the at least one observation and the at least one action to determine a recommendation.

17. The method of claim 11, wherein the generating further comprises using a natural processing engine to generate tags.

18. The method of claim 11, wherein the predicting is based on pre-configured rules.

19. The method of claim 11, wherein a browser-plug is configured to receive the request for a recommendation.

20. A non-transitory computer readable medium storing a set of instructions that are executable by one or more processors of a system to cause the system to perform operations for performing a real-time recommendation process, the operations comprising:
   receiving a request for a benefit recommendation;
   generating at least one tag based on input data associated with the received request and based on predefined rules that are associated with a list of pre-defined conditions;
   extracting at least one keyword from the input data using the at least one generated tag;
   identifying based on the at least one extracted key word at least one condition corresponding to the list of pre-defined conditions;
   parsing mapping data to identify at least one observation and at least one action based on the at least one identified condition, wherein the mapping data associates observations with actions;
   predicting at least one recommendation based on the identified at least one observation and the identified at least one action in real time; and
   providing the at least one predicted recommendation for display to a user device, wherein the at least one predicted recommendation includes a preferred recommendation.

* * * * *